US011660102B2

(12) United States Patent
Akhlaghpour et al.

(10) Patent No.: US 11,660,102 B2
(45) Date of Patent: *May 30, 2023

(54) METHOD OF CONTROLLING INSTRUMENTATION DEPTH IN TOTAL JOINT ARTHROPLASTY

(71) Applicant: THINK SURGICAL, INC., Fremont, CA (US)

(72) Inventors: Hosna Akhlaghpour, Fremont, CA (US); Ryan Sass, Fremont, CA (US); Kyle Kuznik, Fremont, CA (US); Micah Forstein, Fremont, CA (US); Gibson Elliot, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/948,333

(22) Filed: Sep. 20, 2022

(65) Prior Publication Data

US 2023/0019609 A1    Jan. 19, 2023

Related U.S. Application Data

(63) Continuation of application No. 16/757,381, filed as application No. PCT/US2018/056569 on Oct. 18, 2018, now Pat. No. 11,457,933.

(Continued)

(51) Int. Cl.
*A61B 17/16* (2006.01)
*A61B 34/30* (2016.01)
(Continued)

(52) U.S. Cl.
CPC .......... *A61B 17/1666* (2013.01); *A61B 34/30* (2016.02); *A61F 2/4609* (2013.01);
(Continued)

(58) Field of Classification Search
CPC ............... A61B 17/1666; A61B 34/30; A61B 2034/102; A61B 2034/105;
(Continued)

(56) References Cited

U.S. PATENT DOCUMENTS

2011/0082462 A1* 4/2011 Suarez ................. A61B 17/162
606/130
2011/0152871 A1 6/2011 Park et al.
(Continued)

FOREIGN PATENT DOCUMENTS

WO    2017123506 A1    7/2017

OTHER PUBLICATIONS

Int'l. Search Report for PCT/US2018/056569, dated Mar. 7, 2019.

*Primary Examiner* — Zade Coley
*Assistant Examiner* — Diana Jones
(74) *Attorney, Agent, or Firm* — MaxGoLaw PLLC

(57) ABSTRACT

A method to guide in preparation of a bone relies on an instrument having a shaft with a working end and a stop member. The shaft is free to translate along an axis. Surgical planning data is registered to the bone to determine intraoperative coordinates of the desired axis and depth. The instrument holder is positioned by the bone so the stop member contacts the instrument holder to prevent translating beyond the desired depth. Alternatively, an arm is manipulated to align the instrument with the desired axis. The working end rests on the bone to define a linear separation to the desired depth. By proximally translating the instrument holder to contact the stop member and distally translating the instrument holder along the shaft, the stop member physically stops translating beyond the desired depth. A surgical system for performing the methods is provided; a reamer or impactor are also disclosed.

20 Claims, 7 Drawing Sheets

Related U.S. Application Data

(60) Provisional application No. 62/574,429, filed on Oct. 19, 2017.

(51) Int. Cl.
| | | |
|---|---|---|
| *A61F 2/46* | (2006.01) | |
| *A61B 34/10* | (2016.01) | |
| *A61B 34/20* | (2016.01) | |
| *A61B 34/32* | (2016.01) | |
| *A61B 34/37* | (2016.01) | |
| *A61B 34/00* | (2016.01) | |
| *A61B 90/00* | (2016.01) | |
| *A61B 17/00* | (2006.01) | |
| *A61B 17/56* | (2006.01) | |

(52) U.S. Cl.
CPC .............. *A61B 34/32* (2016.02); *A61B 34/37* (2016.02); *A61B 2017/00973* (2013.01); *A61B 2017/564* (2013.01); *A61B 2034/102* (2016.02); *A61B 2034/105* (2016.02); *A61B 2034/2055* (2016.02); *A61B 2034/742* (2016.02); *A61B 2034/743* (2016.02); *A61B 2034/744* (2016.02); *A61B 2090/034* (2016.02); *A61F 2002/4633* (2013.01); *A61F 2002/4681* (2013.01)

(58) Field of Classification Search
CPC . A61B 2034/2055; A61B 34/32; A61B 34/37; A61B 2034/742; A61B 2034/743; A61B 2034/744; A61B 2090/034; A61B 2017/00973; A61B 2017/564; A61F 2/4609; A61F 2002/4633; A61F 2002/4681

See application file for complete search history.

(56) References Cited

U.S. PATENT DOCUMENTS

| | | |
|---|---|---|
| 2012/0209277 A1 | 8/2012 | Leparmentier et al. |
| 2014/0207139 A1 | 7/2014 | Smith et al. |
| 2017/0196711 A1 | 7/2017 | Behzadi ............... A61B 17/142 |

* cited by examiner

METHOD OF CONTROLLING INSTRUMENTATION DEPTH IN TOTAL JOINT ARTHROPLASTY

RELATED APPLICATIONS

This application is a continuation of U.S. application Ser. No. 16/757,381, filed Apr. 18, 2020, that in turn as US National Phase application of PCT/US2018/056569, filed Oct. 18, 2018, that in turn claims priority benefit of U.S. Provisional Application Ser. No. 62/574,429, filed Oct. 19, 2017; the contents of which are hereby incorporated by reference.

FIELD OF THE INVENTION

The present invention generally relates to the field of computer-assisted orthopedic surgery, and more particularly to controlling instrumentation depth when preparing a bone or implanting a prosthesis during total joint arthroplasty.

BACKGROUND OF THE INVENTION

In the field of orthopedics, total joint arthroplasty (TJR) involves the replacement of a subject's joint with prosthetic components. In particular, total hip arthroplasty (THA) requires the implantation of both a femoral component and an acetabular component. Traditionally, a surgeon pre-operatively determines the position and orientation (POSE) of the components before the prosthesis is seated or implanted. The surgeon then uses manual instruments to prepare the bones to receive the implants in the planned POSE. Unfortunately, this approach can be unpredictable as being subject to the skill of the particular surgeon. Therefore, to improve the implant procedures, computer-assisted surgical systems have become popular to prepare and implant the cup prosthesis more accurately.

One such surgical system for planning and executing a THA procedure is the TSOLUTION ONE® Surgical System (THINK Surgical, Inc., Fremont, Calif.). The TSOLUTION ONE® includes a pre-operative planning workstation for generating a surgical plan, and a robotic surgical device to execute the pre-operative plan intra-operatively. Prior to the procedure, the surgeon pre-operatively plans a desired POSE for the femoral and cup prosthesis using three-dimensional (3-D) bone models of the patient's anatomy and computer-aid design (CAD) files of the prostheses. The plan is then transferred to the robotic device in the operating room (OR). Intra-operatively, the cup procedure begins by fixating the robotic device to the anatomy with the use of pins that are screwed into the bone of a patient. After the fixation step, the bone is registered to the robotic device, which transforms the position of the bone and the coordinates of the surgical plan to the robotic coordinate system. The robotic device then positions and constrains a reamer, by way of physical guide attached to the electro-mechanical arm, in the planned orientation to permit the surgeon to prepare the acetabulum. Following the preparation of the acetabulum, an impactor with the cup prosthesis is attached to the electro-mechanical arm. The arm guides and constrains the impactor in the planned orientation while the surgeon applies a series of impaction forces on the impactor to implant the cup prosthesis.

However, in conventional systems, the electro-mechanical arm only aligns and constrains the reamer and impactor along the planned orientation, and as a result, the reamer and impactor are free to translate along that planned orientation. As the reamer and impactor are free to translate, the surgeon may unintentionally under-ream the cup, over-ream the cup, implant the prosthesis too proud or too low, all of which may result in sub-optimal patient outcomes and decreased implant longevity.

Therefore, there is a need in the art for a system and method to provide guidance, feedback, and/or physical stops in the preparation of a bone or the implantation of a prosthesis to a desired depth with a semi-manual operated instrument.

SUMMARY OF THE INVENTION

A method to guide a user in preparing a bone of a subject to receive a prosthesis to a desired depth is provided. The method utilizes a robotic surgical system having a manipulator arm, an instrument holder attached to the manipulator arm, and surgical planning data designating a desired axis and depth to implant the prosthesis in the bone. An instrument is provided having a shaft with a working end and a stop member proximal to the working end. The shaft is assembled to the instrument holder between the working end and the stop member such that the shaft is free to translate along a longitudinal axis of the instrument relative to the instrument holder. Surgical planning data is registered to the bone to determine intra-operative coordinates of the desired axis and depth. The instrument holder is positioned at a position proximal to the bone such that the stop member contacts the instrument holder to prevent the instrument from being translated beyond the desired depth.

A method to guide a user in preparing a bone of a subject to receive a prosthesis to a desired depth is provided. The method utilizes a robotic surgical system having a manipulator arm, an instrument holder attached to the manipulator arm, and surgical planning data designating a desired axis and depth to implant the prosthesis in the bone. An instrument is provided having a shaft with a working end and a stop member proximal to the working end. The shaft is assembled to the instrument holder between the working end and the stop member such that the shaft is free to translate along a longitudinal axis of the instrument relative to the instrument holder. Surgical planning data is registered to the bone to determine intra-operative coordinates of the desired axis and depth. The arm is manipulated to the desired axis so the longitudinal axis of the instrument aligns with the desired axis. The working end rests on an outer surface of the bone to define a linear separation between the working end resting on a surface of the bone and the desired depth to implant the prosthesis. By proximally translating the instrument holder to contact the stop member and distally translating the instrument holder along the shaft by a distance corresponding the linear separation, the stop member contacts the instrument holder to physically stop the instrument from being translated beyond the desired depth.

A surgical system for performing the above methods includes a surgical robot, a workstation including a computer, user-peripherals, and a monitor for displaying the graphical user interface (GUI). The computer includes a processor, non-transient storage memory, and other hardware, software, data and utilities to execute the method. The user peripherals allow a user to interact with the GUI and include user inputs via at least one of a keyboard, mouse, or a touchscreen capability on the monitor.

A reamer or impactor instrument for preparing a bone of a subject to receive a prosthesis to a desired depth utilizing a robotic surgical system includes a shaft having a working end and a stop member proximal to the working end. The shaft is adapted to attach to an instrument holder of a surgical robot between the working end and the stop member where the shaft is free to translate along a longitudinal axis of the instrument relative to the instrument holder such that the stop member will contact the instrument holder to prevent the instrument from being translated beyond the desired depth.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 2A depicts a reamer having a handle to act as a stop member, and FIG. 2B depicts a reamer having an added stop member;

DETAILED DESCRIPTION OF THE INVENTION

Figure 1:
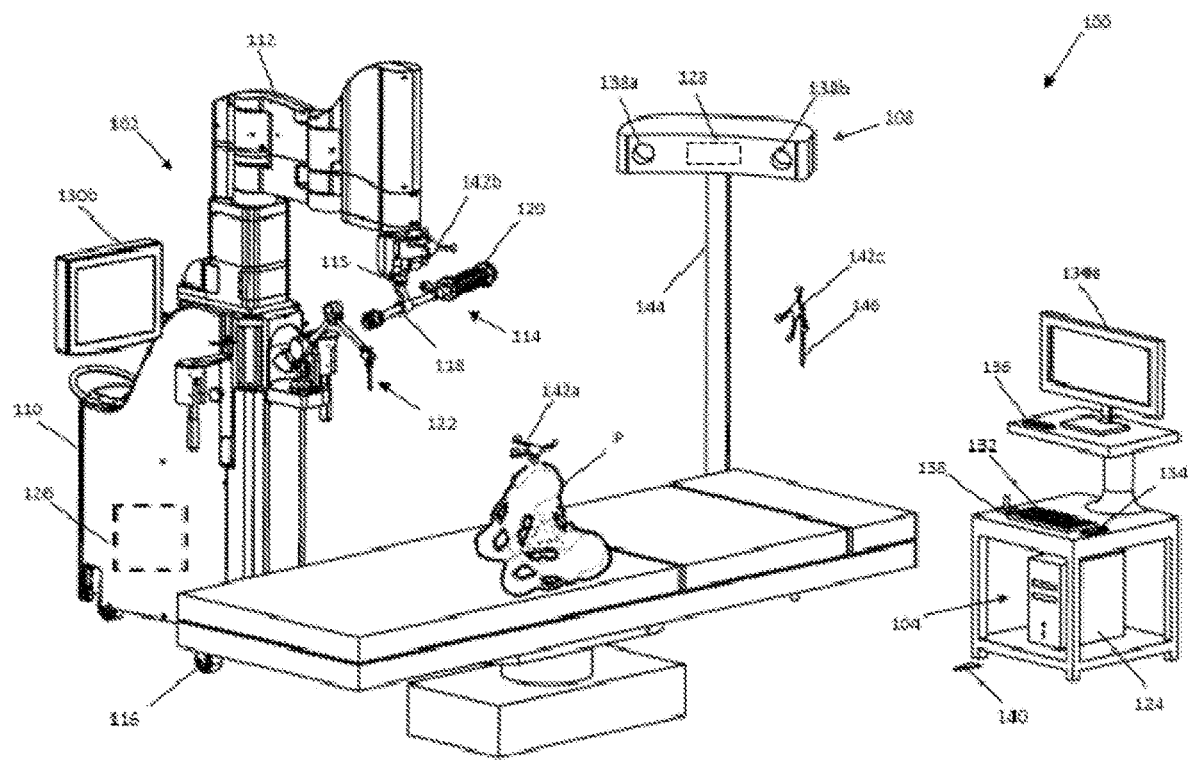
FIG. 1 depicts a surgical system for controlling instrumentation depth in the context of an operating room in accordance with embodiments of the invention.

The present invention has utility as a system and method for providing guidance, feedback, physical stops, or a combination thereof to prepare a bone to a desired depth or implant a prosthesis to a desired depth with a semi-manual operated instrument. The system and methods are particularly useful in the preparation of the acetabular cup and implantation of a cup prosthesis in total hip arthroplasty (THA) using a semi-manual operated reamer or impactor that are physically constrained along a planned orientation with a surgical robot. However, it should be appreciated that although the system and methods are described herein in the context of cup preparation during THA, the system and methods may also apply to other orthopedic applications such as pedicle screw placement during spine surgery, pin placement in bone fracture reconstruction, maxillofacial reconstruction, cranial surgery, ligament reconstruction surgery, and other procedures requiring precision and accuracy along a depth axis or plane (i.e., an axis or plane oriented into the body). It is further appreciated, a miniaturized tool associated with an inventive system is amenable to repair of metatarsal, metacarpal and otic bone structures that are currently difficult to address surgically.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references mentioned herein are incorporated by reference in their entirety.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

As used herein, the term "semi-manual" in the context of an operational instrument refers to an instrument that is not fully automated to operate. For example, a semi-manual operated reamer, or semi-manual operated drill-bit, may be constrained in a planned orientation by an autonomous surgical robot where a user manually translates the reamer or drill-bit along the planned orientation and drives the reamer or drill-bit with a manually operated drill.

As used herein, the term "digitizer" refers to a measuring device capable of measuring physical coordinates in three-dimensional space. For example, the "digitizer" may be: a "mechanical digitizer" having passive links and joints, illustratively including the high-resolution mechanical sensor arm described in U.S. Pat. No. 6,033,415; a non-mechanically tracked digitizer probe (e.g., optically tracked, electromagnetically tracked, acoustically tracked, and equivalents thereof) as described in for example U.S. Pat. No. 7,043,961; or an end-effector of a surgical robot.

As used herein, the term "digitizing" refers to the collecting, measuring, and/or recording of physical points in space with a digitizer.

As used herein, the term "pre-operative bone data" refers to bone data used to pre-operatively plan a procedure before making modifications to the actual bone. The pre-operative bone data may include one or more of the following: a patient's actual exposed bone prior to modification; a 2-D image data set of a bone; a 3-D virtual generic bone model; a physical bone model; a 3-D virtual patient-specific bone model; a set of data collected directly on a bone intra-operatively commonly used with imageless computer-assist devices; or a combination thereof.

As used herein, the term "registration" refers to the determination of the POSE and/or coordinate transformation between two or more objects or coordinate systems such as a computer-assisted device, a bone, pre-operative bone data, surgical planning data (i.e., an implant model, cut-file, virtual boundaries, virtual planes, or other tissue modification instructions associated with or defined relative to the pre-operative bone data), and any external landmarks (e.g., a fiducial marker array) associated with the bone, if such landmarks exist. Methods of registration are well known in the art illustratively including the methods described in U.S. Pat. Nos. 6,033,415, 8,010,177, and 8,287,522.

As used herein, the term "translation" or "translating" refers to a movement that is only along an axis.

Embodiments of the present invention describe a system and methods for providing guidance, feedback, and/or physical stops to aid a user in preparing a bone or implanting a prosthesis to a desired depth with a semi-manual operated instrument. Examples of systems, and more specifically robotic surgical systems that may be adapted or modified with the inventive embodiments described herein include the TSolution One Surgical System (THINK Surgical, Inc., Fremont, Calif.) as generally described in U.S. Pat. No. 5,086,401, the RIO Robotic Arm Interactive Orthopedic System (Stryker-Mako, Fr. Lauderdale Fla.) as described in U.S. Pat. No. 8,010,180, the ROSA Surgical System (Zimmer-Biomet, Warsaw, Ind.) as described in U.S. Pat. No. 9,237,861, as well as other serial-chain manipulators, parallel manipulators, hand-held manipulators, or master-slave robotic systems having autonomous, semi-autonomous, or haptic control.

Exemplary Surgical System

Referring now to the figures, FIG. 1 illustrates a specific inventive embodiment of a robotic surgical system 100 for preparing a bone to a desired depth, or implanting a prosthesis to a desired depth. The surgical system 100 generally includes a surgical robot 102, a computing system 104, and may include at least one of a mechanical digitizer 122 or a non-mechanical tracking system 108.

The surgical robot 102 in some embodiments includes a moveable base 110, a manipulator arm 112 connected to the base 110, and an end-effector assembly 114 removably attached to a distal end of the manipulator arm 112 by way of a flange or coupler 115. The base 110 may include an actuator to adjust the height of the surgical robot 102. The base 110 may further include a set of wheels 116 to maneuver the base 110, which may be fixed into position using a braking mechanism such as a hydraulic brake. The manipulator arm 112 includes various joints and links to manipulate the end-effector assembly 114 in one or more degrees of freedom. The joints illustratively include prismatic, revolute, spherical, or a combination thereof. The end-effector assembly 114 generally includes an instrument holder 118 for holding and/or operating an instrument 120. The surgical robot 102 may further include a mechanical digitizer 122 mounted to the base 110.

The computing system 104 generally includes a planning computer 124; a device computer 126; a tracking computer 128 if a tracking system 108 is present; and peripheral devices. The planning computer 124, device computer 126, and tracking computer 128, may be separate entities, single units, or combinations thereof depending on the surgical system. For example, the device computer 126 may execute all of the operations for the tracking system 108 that would otherwise be performed on a tracking computer 128. The peripheral devices allow a user to interface with the surgical system components and may include: one or more graphical user interfaces (GUI) displayed on a monitor (130a, 130b), and user-input mechanisms illustratively including a keyboard 132, mouse 134, pendent 136, joystick 138, foot pedal 140, or the monitor 130 in some inventive embodiments has touchscreen capabilities.

The planning computer 124 contains hardware (e.g., processors, controllers, and/or memory), software, data, and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan includes surgical planning data/instructions defined relative to the pre-operational bone data to modify the bone. The planning data/instructions may include, for example: a set of cutting parameters (e.g., points, vectors, velocities and acceleration instructions) of a cut-file to autonomously modify a volume of bone; an axis or plane to align an instrument to modify the bone coincident with that axis or plane; a set of virtual boundaries to haptically constrain an instrument within those boundaries to modify the bone; a set of axes, planes, or drill holes to drill pins or screws into the bone; or a graphically navigated set of instructions to modify the bone. The data generated from the planning computer 124 may be transferred to the device computer 126 and/or tracking computer 128 through a wired or wireless connection in the operating room (OR); or transferred via a non-transient data storage medium (e.g., a compact disc (CD), a portable universal serial bus (USB) drive) if the planning computer 124 is located outside the OR.

The device computer 126 in some inventive embodiments is housed in the moveable base 110 and contains hardware, software, data, and utilities that are preferably dedicated to the operation of the surgical robot 102. The device computer 126 may include surgical device control, robotic manipulator control, the processing of kinematic and inverse kinematic data, the execution of registration algorithms, the execution of calibration routines, the execution of the surgical planning data, coordinate transformation processing, providing workflow instructions to a user, communicating with the mechanical digitizer 122 to collect and transform points, and utilizing POSE data from the tracking system 108, if present.

The optional tracking system 108 of the surgical system 100 in some inventive embodiments include two or more optical receivers (138a, 138b) to detect the position of fiducial markers (e.g., retroreflective spheres, active light emitting diodes (LEDs)) uniquely arranged on rigid bodies. The fiducial markers arranged on a rigid body are collectively referred to as a fiducial marker array 142, where each fiducial marker array 140 has a unique arrangement of fiducial markers, or a unique transmitting wavelength/frequency if the markers are active LEDs to distinguish one marker array from another. An example of an optical tracking system is described in U.S. Pat. No. 6,061,644. The tracking system 108 may be built into a surgical light, located on a boom, a stand 144, or built into the walls or ceilings of the OR. The tracking system computer 128 may include tracking hardware, software, data and utilities to determine the POSE of objects (e.g., pelvis P, surgical robot 102) in a local or global coordinate frame. The POSE of the objects is collectively referred to herein as POSE data, where this POSE data may be communicated to the device computer 126 through a wired or wireless connection. Alternatively, the device computer 126 may determine the POSE data using the position of the fiducial markers detected from the optical receivers (138a, 138b) directly.

The POSE data is determined using the position data detected from the optical receivers (138a, 138b) and operations/processes such as image processing, image filtering, triangulation algorithms, geometric relationship processing, registration algorithms, calibration algorithms, and coordinate transformation processing. For example, the POSE of a optically tracked digitizer probe 146 with an attached probe fiducial marker array 142c may be calibrated such that the probe tip is continuously known as described in U.S. Pat. No. 7,043,961. The POSE of an instrument tip or instrument axis of the instrument 120 may be known with respect to a robot fiducial marker array 142b using a calibration method as described in U.S. Prov. Pat. App. 62/128,857. The robot fiducial marker array 142b is depicted on the manipulator arm 112 but may also be positioned on the base 110 or end-effector assembly 114. Registration algorithms may be executed to determine the POSE and coordinate transforms between a bone (e.g., pelvis P), pre-operative bone data, a fiducial marker array 142a, a surgical plan, a surgical robot 102, and/or tracking system 108 using the registration methods as described above.

The POSE data from the tracking system 108 in some embodiments are used by the computing system 104 during the procedure to update the bone and surgical plan coordinate transforms relative to the end-effector assembly 114 so the surgical robot 102 can accurately execute the surgical plan in the event any bone motion occurs. It should be appreciated that in certain embodiments, other tracking systems to track the bone in real-time may be incorporated with the surgical system 100 such as an electromagnetic field tracking system or the mechanical digitizer 122.

In a particular inventive embodiment, the surgical system 100 does not include a tracking system 108 or other sensors to track the bone in real-time, but instead employs a bone fixation system to fix the bone directly to the surgical robot 102, a mechanical digitizer 122 for digitizing, and a bone motion monitoring system to monitor bone motion beyond a pre-determined amount during the procedure, such as the system described in U.S. Pat. No. 5,086,401.

Figure 2A:
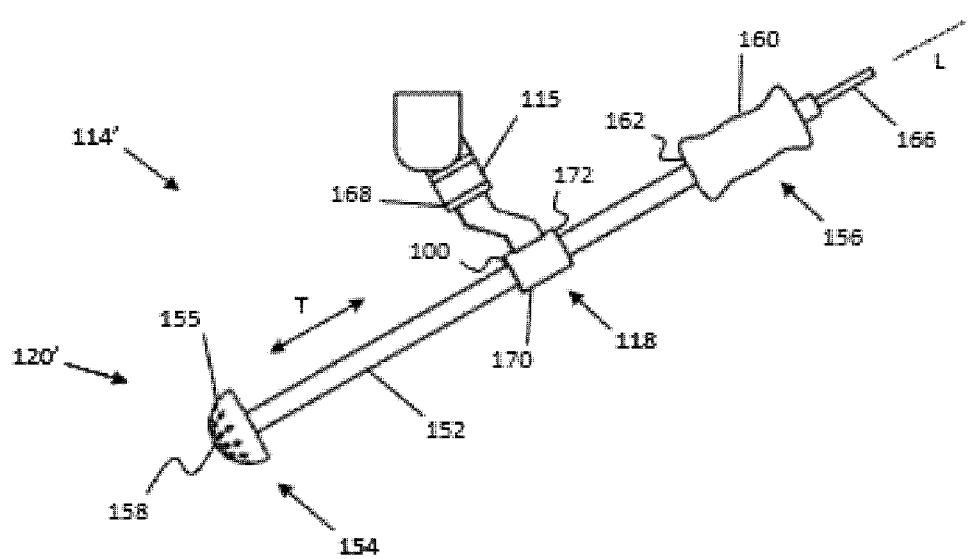
FIGS. 2A and 2B depict detailed views of an instrument holder and an instrument of the surgical system of FIG. 1 in accordance with embodiments of the invention, where
Figure 2B:
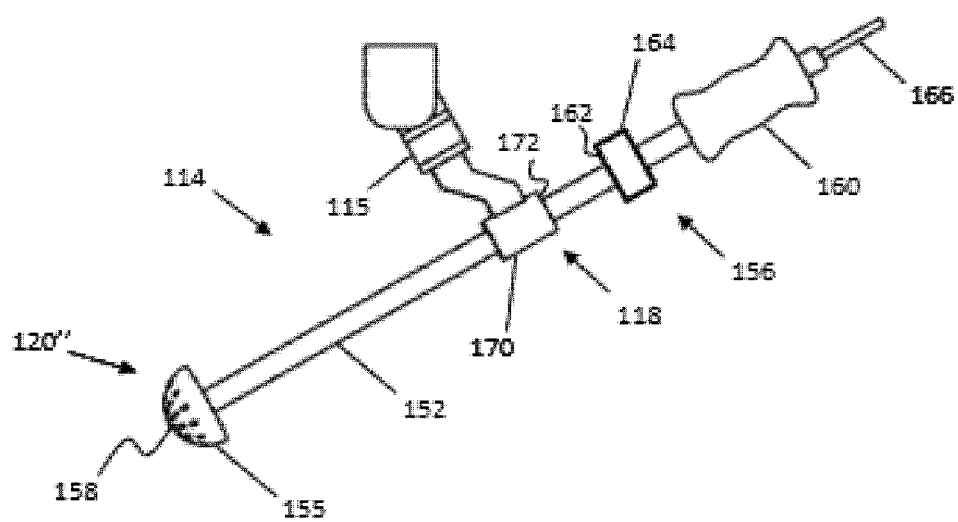

With reference to FIGS. 2A and 2B, a particular inventive embodiment of an end-effector assembly 114' for controlling the depth of an instrument 120' is shown. The end-effector assembly 114' generally includes an instrument holder 118 and the instrument 120' assembled to the instrument holder 118. In the particular inventive embodiment shown in FIGS. 2A and 2B, the instrument shown generally as instrument 120 in FIG. 1 is a reamer 120' (as illustrated throughout the figures) for preparing the acetabular cup during THA. However, it should be appreciated that the instrument 120 may be a drill-bit for drilling bone, a pedicle screw for spinal surgery, a bone screw or pin for bone fractures, a broach for creating cavities, or other semi-manual operated instruments. The instrument 120' generally includes a shaft 152 having a working end 154, a stop member 156 proximal to the working end 154, and a longitudinal axis 'L'. The working end 154 may either be: a) a tool to perform work on the bone illustratively including a grater 155 of a reamer 120', flutes of a drill bit; or b) a prosthesis to be implanted into the bone, illustratively including a cup prosthesis or pedicle screw. The working end 154 further includes a tool center point 158 (or prosthesis center point) defined as the center and most distal portion of the working end 154. With reference to FIG. 2A, the stop member 156 may be a handle 160 of the instrument 120', the handle 160 having a distal stop end 162. In another embodiment, with reference to FIG. 2B, the stop member 156 is a body 164 having at least a portion of its geometry (e.g., diameter, or a protrusion) greater than the shaft 152. The body 164 is positioned between the handle 160, or a proximal end 166 of the instrument 120", and the working end 154 of the instrument. The body 164 may be adjustable along the length of the shaft 152, or fixedly attached or integral to the shaft 152 at a specific position on the shaft 152. The body 164 likewise has a distal stop end 162.

The instrument holder 118 of FIG. 2A includes a mount 168 to couple to the distal end of the manipulator arm 112 by way of a coupler 115, and an instrument assembly portion 170 for assembling the instrument 120' thereto. In a particular inventive embodiment, the instrument assembly portion 170, with the aid of the manipulator arm 112, is configured to support and hold the instrument (120', 120") along a fixed axis (e.g., anteversion/inclination axis for cup reaming, a desired axis for a pedicle screw, the longitudinal axis 'L' of the instrument 120'), while permitting a user to at least one of: a. manually translate the instrument 120' along the fixed axis (as shown by the arrow 'T'); and/or b. manually rotate the instrument 120' about the fixed axis. The instrument assembly portion 170 may be a body having a receiving opening, a clasp, a latch, or a flange having fixation elements such as threads, to receive the instrument (120', 120") thereon. In a particular embodiment, the instrument assembly portion 170 is a linear bearing that receives the instrument (120', 120") there through to permit manual translation and/or rotation of the instrument (120', 120"). It is worth noting, that the 'manual rotation' may be performed by a user's hands, or by a secondary device such as a manually operated drill. For example, a reamer 120' may have a proximal end 166 configured to be received in a drill chuck of a drill, where a user may manually operate the drill to 'manually rotate' a grater 155 of the reamer 120'. The instrument assembly portion 170 further includes a proximal stop end 172 configured to make contact with the distal stop end 162 of the stop member 156 to restrict linear motion of the instrument (120', 120") to aid in the control of the depth of the instrument (120', 120"), which is further described in more detail below.

Surgical Planning

Figure 3:
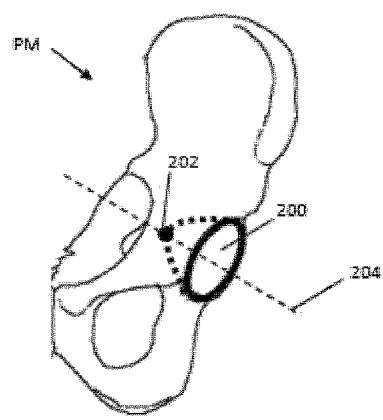
FIG. 3 depicts a three-dimensional virtual model of a pelvis.

Generally, the user plans the POSE of a prosthesis model relative to pre-operative bone data in a pre-operative planning software program having a graphical user interface (GUI). In a particular embodiment, with reference to FIG. 3, the pre-operative bone data is a virtual three-dimensional (3-D) bone model, such as a 3-D pelvis model (PM), generated from an image data set of a subject's anatomy. The image data set may be collected with an imaging modality such as computed tomography (CT), magnetic resonance imaging (MRI), X-ray scans, ultrasound, or a combination thereof. The 3-D bone model(s) are readily generated from the image data set using medical imaging software such as Mimics® (Materialise, Plymouth, Mich.) or other techniques known in the art such as the one described in U.S. Pat. No. 5,951,475. A set of 3-D computer aided designs (CAD) models of the manufacturer's prostheses (prostheses models) are pre-loaded in the software, such as a cup prosthesis model 200, that allows the user to place the components of a desired prosthesis to the 3-D bone model of the boney anatomy to designate the best fit, position, orientation, and depth of the prosthesis to the bone. The user can then save this surgical planning data to an electronic medium that is loaded and read by a computer-assisted device to assist the surgeon intra-operatively to prepare the bone to receive the physical prosthesis according to the plan.

In a specific inventive embodiment, the user plans a desired depth, and axis 204 (e.g., desired anteversion angle and inclination angle) of a cup prosthesis model 200 relative to a patient-specific 3-D pelvis model (PM). As used herein, a 'desired axis', such as desired axis 204, refers to both the orientation of the axis and the position of the axis relative to the anatomy. The cup prosthesis model 200, and corresponding cup prosthesis, includes an apex 202, defined as the deepest portion of the prosthesis that contacts the bone along a desired axis. It should be appreciated, that the apex of a pedicle screw for example, would correspond to the distal tip of the screw according to this definition of 'apex'. In other embodiments, the user plans the position for a cup prosthesis using other pre-operative data, such as a 2-D image data set, or a model of the bone generated intra-operatively from a cloud of points collected directly on the exposed bone. In any case, the surgical planning data preferably includes at least a desired axis for the prosthesis, and the desired depth for the prosthesis. In a specific inventive embodiment, the desired depth for the prosthesis is defined by the intersection of the apex 202 of the prosthesis with the pre-operative bone data. It is also appreciated, that a user may designate a depth for the prosthesis on the pre-operative bone data directly using software widgets or tools without the use of a prosthesis model. The surgical planning data, with the desired axis and depth, is then transferred, wired or wirelessly, to the device computer 126 and/or tracking computer 128 to prepare a bone and/or implant a prosthesis along the desired axis and depth as further described below.

Intraoperative Depth Control

Figure 4:
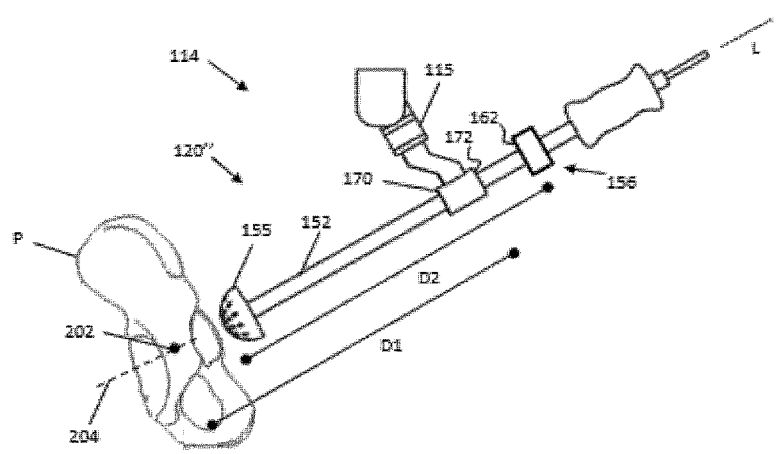
FIG. 4 depicts an instrument holder supporting a reamer and positioned relative to an acetabulum to control reaming depth in accordance with embodiments of the invention.

With reference to FIG. 1 and FIG. 4, an example of several methods for controlling the depth of an instrument during total joint arthroplasty with a robotic surgical system 100 is illustrated in the context of acetabular cup preparation during total hip arthroplasty. Intraoperatively, the acetabulum of the pelvis (P) is exposed using conventional incision techniques. In one inventive embodiment, a tracking array 142*a* is fixed to a portion of the pelvis (P) to track any motion of the pelvis during the procedure with a tracking system 108. In an alternative inventive embodiment, one or more fixation pins are drilled into the pelvis and assembled to the surgical robot 102 with a series of fixation rods to rigidly fix the pelvis (P to the robot 102. Subsequently, at least two of the pelvis (P), pre-operative bone data, surgical planning data, and any landmarks associated with the pelvis (P) (e.g., tracking array 142*a*), are registered to the surgical robot 102 using the aforementioned registration techniques. If an imageless computer-assist device is used, the user may collect several points in and around the acetabulum of the pelvis (P) to create a point cloud representation of the acetabulum. During the point collection, the bone is inherently registered to the computer-assist device, where the user may then plan the placement of the prosthesis relative to the point cloud representation. The registration step provides the surgical system 100 with the intraoperative coordinates for the desired axis 204 and the desired depth 202 to implant the prosthesis in the acetabulum as defined in the surgical plan.

A reamer 120", as described above, is assembled to the instrument assembly portion 170 and autonomously manipulated, by way of the manipulator arm 112, such that the longitudinal axis 'L' of the reamer 120' aligns with the desired axis 204 defined in the plan. Preferably, the reamer 120' is positioned proximal to the pelvis 'P' along the desired axis 204 such that the reamer 120' does not contact the anatomy. After the longitudinal axis 'L' of the reamer 120' is aligned with the desired axis 204, the reaming depth may be controlled by several different methods.

In a particular inventive embodiment of a method for controlling the depth of the reamer 120" with the axes 'L' and 204 aligned, the surgical robot 102 generally positions the instrument holder 118 at a position proximal to the bone such that the stop member 156 will contact the instrument holder 118 to prevent the reamer 120" from being translated beyond the desired depth. More specifically, the length from the distal stop end 162 of the stop member 156 to the tool center point 158 is known and stored in the computing system 104. The proximal stop end 172 of the instrument assembly portion 170 is also known by programming the geometry of the instrument holder 118 as a link in the kinematic chain of the manipulator arm 112. The surgical robot 102 also knows the coordinates of the desired depth (i.e., the planned position of the apex 202) in the robotic or tracking system coordinate frame from the registration. Therefore, the surgical robot 102 can position the proximal stop end 172 of the instrument holder 118 at a distance D1 from the desired depth such that the distance D1 is equal to a distance D2, where the distance D2 corresponds to the known distance between the distal stop end 162 of the stop member 156 and the tool center point 158. As the user reams the acetabulum and translates the reamer 120" towards the desired depth, the distance between the distal stop end 162 and proximal stop end 172 decreases. Once the user reaches the desired depth, the proximal stop end 172 of the instrument holder 118 makes contact with the distal stop end 162 of the stop member 156, thereby physically stopping the user from over-reaming the acetabulum. If the user needs multiple reamers with graters 155 of increasing diameter, then the distance D2 of the distal stop member 162 relative to the tool center point 158 should be consistent from reamer to reamer; however, this consistent distance is not absolutely necessary if the user performs a few additional steps as described below (e.g., digitizing the tool center point 158 and/or one or more points on the distal portion 162 of the stop member 156). After reaming is complete, an impactor for impacting a cup prosthesis into the acetabulum is assembled to the instrument assembly portion 170 and the process is repeated to ensure the cup prosthesis is implanted to the desired depth.

Figure 5:
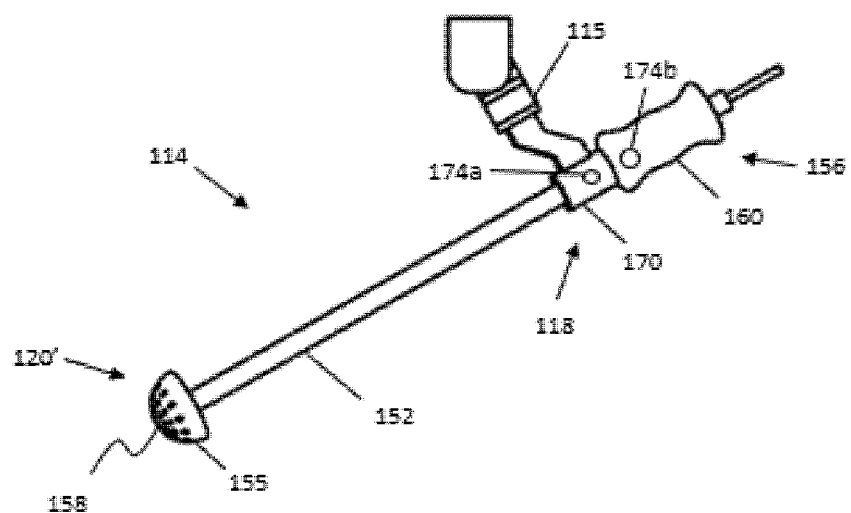
FIG. 5 depicts an instrument holder in contact with a stop member of the instrument in accordance with embodiments of the invention.

In another inventive embodiment of a method for controlling the depth with the axes 'L' and 204 aligned, a user may first rest the grater 155 on the outer edge of the acetabulum. The instrument holder 118 is then translated, manually or automatically, along the desired axis 204 in a proximal direction towards the stop member 156, with the grater 155 still resting on the acetabulum, until the proximal stop end 172 makes contact with the distal stop end of the stop member 156. The configuration of the proximal stop end 172 of the instrument assembly portion 170 in contact with the distal stop end of handle 160 is shown in FIG. 5, where the stop member is a handle 160 of the reamer 120'. Next, a signal is sent to the computing system 104 to notify the system of the contact. In one inventive embodiment, the user signals to the computing system 104, by way of a user input mechanism or signal to the tracking system, that the proximal stop end 172 of the instrument assembly portion 170 and distal stop end distal stop end of handle 160 are in contact. In another inventive embodiment, the stop member 156 and/or instrument assembly portion 170 may include one or more contact sensor(s) (174*a*, 174*b*) to automatically communicate the contact to the computing system 104.

Next, a length of a margin is determined, the margin being the distance between the current position of the tool center point 158 resting on the outer edge of the acetabulum and the desired depth (the planned position of the apex 202). The length of the margin may be determined during surgical planning by defining a circle to represent the outer edge of the acetabulum on the pelvis virtual model (PM), and then determining the center of that circle. Then, the planning software may calculate the distance of the margin as the distance between the center of that circle and the apex 202 of the planned prosthesis placement. Here, the length of the distal stop end 162 of the stop member 156 and the tool center point 158 may not necessarily be known, nor may the position of the proximal stop end 172 of the instrument holder 118 be known in the robotic system coordinates. In another inventive embodiment, the computing system 104 can calculate the length of the margin if: a) the length between the distal stop end 162 of the stop member 156 and the tool center point 158 is known in the computing system 104; b) the proximal stop end 172 of the instrument holder 118 is known and programmed as a link in the kinematic chain of the robot; and c) the desired depth is known in the robotic or tracking system coordinate system from registration. After the length of the margin is determined, the instrument holder 118 is translated, manually or automatically, along the desired axis 204 in a distal direction towards the pelvis (P), with the grater 155 still resting on the acetabulum, by the determined distance of the margin. The instrument holder 118 is then rigidly held at this location during the reaming process. As the user reams the acetabulum and translates the reamer 120' towards the desired depth, the distance between the distal stop end and proximal stop end 172 decreases. Once the user reaches the desired depth, the proximal stop end 172 of the instrument holder 118 makes contact with the distal stop end 162 of the stop member 156 or in contact with the distal stop end of handle 160, thereby physically stopping the user from over-reaming the acetabulum.

With reference to FIG. 4, another inventive embodiment of a method for controlling the depth of the reamer 120' with the axes 'L' and 204 aligned includes a step-wise advancement of the reamer 120" toward the desired depth facilitated by the surgical robot 102. First, the surgical robot 102 aligns the axes 'L' and 204 and positions the instrument holder 118 at a position proximal to the bone. A user then translates the reamer 120" towards the bone to engage the stop member 156 with the instrument holder 118. The user may then digitize the tool center point 158 to determine the distance between the tool center point 158 and the instrument holder 118. In other inventive embodiments, the distance between the tool center point 158 and distal portion 162 of the stop member 156 is already known and stored in the computing system 104. Subsequently, the user hand-guides the instrument holder 118, with the stop member 156 and instrument holder 118 engaged, until the grater makes contact or fits into the acetabulum at a position as desired by the user (e.g., a starting reaming position). The user then signals to the computing system 104 that the reamer is at a starting position. Now, because the distance between the instrument holder 118 and tool center point 158 is known, the distance between the tool center point 158 and the desired depth is also known from the registration. The surgical robot 102 may then advance, step-wise, the instrument holder 118 towards the desired depth. The user may signal to the computing system 104 when to advance to the next step, wherein the surgical robot 102 then advances the instrument holder 118 by an 'x' distance (e.g., 1 mm, 2 mm, N mm). The instrument holder 118 and stop member 156 stay engaged throughout the advancement process. The user then has the ability to advance the instrument holder 118 in between reamer 120" changes. Once the reamers 120" reaches the desired depth, the surgical robot 102 ceases to advance, or alerts the user that the desired depth has been reached. In specific inventive embodiments, the computing system 104 may have an override feature that permits the user to continue reaming beyond the desired depth.

Figure 6:
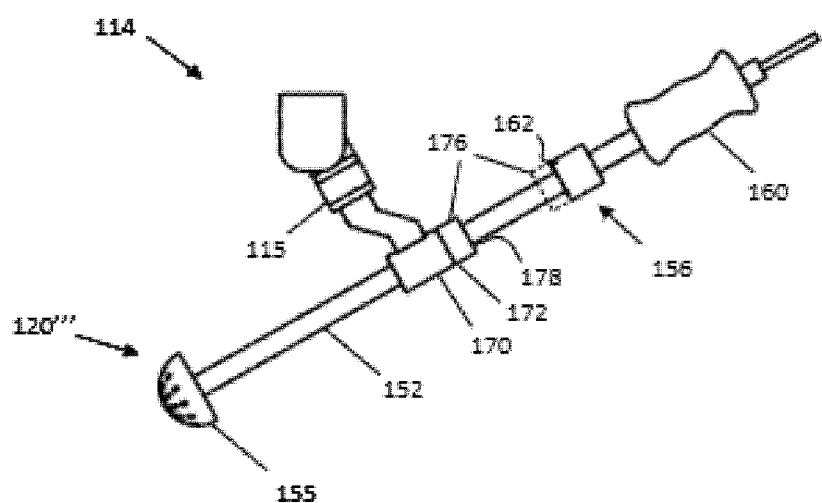
FIG. 6 depicts a suppressing element associated with an instrument holder in accordance with embodiments of the invention.

With reference to FIG. 6, in a particular inventive embodiment, the instrument 120''' and/or the instrument holder 118 may include one or more suppression elements 176 such as a force suppressing springs or elastic padding. The suppression element 176 is configured to dampen or suppress excessive forces that may be transferred to the manipulator arm 112 when the instrument 120''' makes contact with the instrument holder 118. In one inventive embodiment, the suppression element is positioned at the proximal end 172 of the instrument assembly portion 170. In another inventive embodiment, the suppression element 176 (shown in doted lines) may be positioned at distal end 162 of the stop member 156. In a further inventive embodiment, suppression elements 176 are positioned at both locations. Therefore, the components (e.g., motors, encoders) of the manipulator arm 112 are not harmed while the user impacts or reams the acetabulum, especially as the user approaches the desired depth. It should be appreciated however, that if suppression elements 176 are present, then a proximal end 178 of the suppression element 176 must now act as the proximal end 172 of the instrument assembly portion 170 to make many of the aforementioned methods work. Likewise, if a suppression element 176 is positioned on the instrument, then a distal end of the suppression element 176 must now act as the distal end 162 of the stop member 156. In another inventive embodiment, the forces may be suppressed on the manipulator arm using a magnetic holder assembly as described in U.S. Prov. Pat. Ser. No. 62/420,064.

Sensor Based Intraoperative Depth Control

Figure 7:
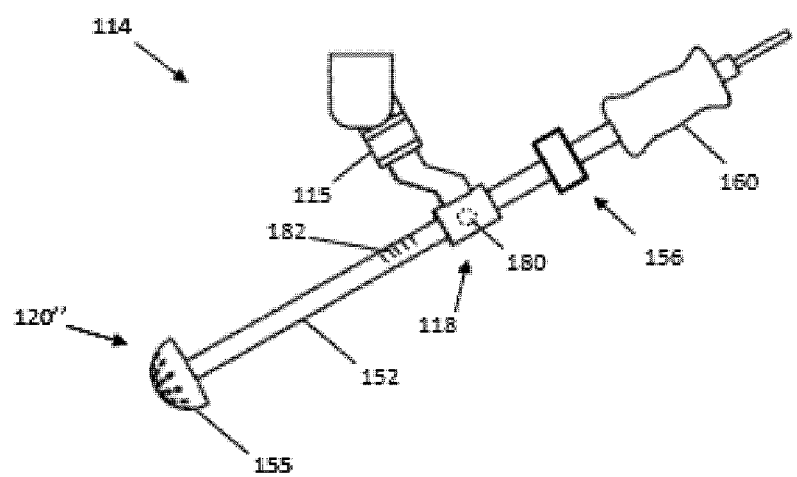
FIG. 7 depicts a depth sensor associated with an instrument holder in accordance with embodiments of the invention.

In a particular inventive embodiment, with reference to FIG. 7, the instrument holder 118 may include one or more depth sensors 180 to monitor and control the depth of the reamer 120". In one inventive embodiment, the depth sensor 180 is a linear variable differential transformer (LVDT). The LVDT may sense the displacement of the shaft 152 of the reamer 120" while the user is reaming. The shaft 152 of the reamer 120" may include core positioned a known distance from the tool center point 158. The surgical robot 102 may then position the instrument holder 118 having the LVDT proximal to the bone such that the LVDT can interact with the core and measure the displacement of the reamer 120' as the user reams the acetabulum. Once the user reaches the desired depth, the computing system 104 may alert the user that the desired depth has been reached.

In another inventive embodiment, the depth sensor 180 is a linear encoder. The shaft 152 of the reamer 120" may include a plurality of indentations or markings readable 182 by the linear encoder. The surgical robot 102 may then position the instrument holder 118 having the linear encoder proximal to the bone such that the linear encoder may read the markings and measure the displacement of the reamer 120" as the user reams the acetabulum. Once the user reaches the desired depth, the computing system 104 may alert the user that the desired depth has been reached.

Other Embodiments

While at least one exemplary inventive embodiment has been presented in the foregoing detailed description, it should be appreciated that a vast number of variations exist. It should also be appreciated that the exemplary inventive embodiment or exemplary inventive embodiments are only examples, and are not intended to limit the scope, applicability, or configuration of the described inventive embodiments in any way. Rather, the foregoing detailed description will provide those skilled in the art with a convenient roadmap for implementing the exemplary inventive embodiment or exemplary inventive embodiments. It should be understood that various changes may be made in the function and arrangement of elements without departing from the scope as set forth in the appended claims and the legal equivalents thereof.

The invention claimed is:

1. A surgical system, comprising:
a surgical robot comprising an instrument holder configured to couple with an instrument having a working end and a stop member located at a position on the instrument that is at a first pre-determined distance from the working end, wherein the instrument is translatable within the instrument holder when coupled to the instrument holder; and
a computer comprising a processor configured to:
control the surgical robot to position the instrument holder at a second pre-determined distance from a pre-determined bone location of a patient wherein the stop member prevents translation of the working end beyond the pre-determined bone location.

2. The system of claim 1 wherein the second pre-determined distance is measured from a proximal end of the instrument holder to the pre-determined bone location.

3. The system of claim 2 wherein the first pre-determined distance is measured from an apex of the working end to a distal end of the stop member.

4. The system of claim 3 wherein the first pre-determined distance is equal to the second pre-determined distance.

5. The surgical system of claim 1 wherein the pre-determined bone location corresponds to a pre-determined depth for implanting a prosthesis in the bone of the patient.

6. The system of claim 5 wherein the computer is further configured to control the surgical robot to orient the instrument holder in a pre-determined orientation with respect to the patient.

7. The system of claim 6 wherein the pre-determined orientation corresponds to a pre-determined orientation for implanting the prosthesis in the bone of the patient.

8. The surgical system of claim 7 further comprising planning software stored in non-transient memory and operatively coupled to a processor for determining a depth and an orientation for implanting the prosthesis in the bone of the patient.

9. The system of claim 1 wherein the instrument is translatable within the instrument holder between the working end and the stop member.

10. The system of claim 1 wherein the stop member contacts the instrument holder when a portion of the working end reaches the pre-determined bone location.

11. The system of claim 10 wherein the portion of the working end is a distal apex of the working end.

12. The surgical system of claim 1 further comprising the instrument.

13. The surgical system of claim 1 wherein the instrument is a reamer and the working end of the reamer is a grater.

14. The surgical system of claim 13 wherein the stop member contacts the instrument holder when a portion of the grater reaches the pre-determined bone location.

15. The surgical system of claim 1 wherein the instrument is an impactor and the working end of the impactor is a prosthesis.

16. The surgical system of claim 15 wherein the stop member contacts the instrument holder when a portion of the prosthesis reaches the pre-determined bone location.

17. The surgical system of claim 1 wherein the instrument comprises a handle, wherein a distal end of the handle is the stop member.

18. The surgical system of claim 1 wherein the stop member is positioned along an axis of the instrument between a handle of the instrument and the working end.

19. The surgical system of claim 1 further comprising a force suppressing spring or elastic padding positioned on a distal end of the stop member or a proximal end of the instrument holder.

20. The surgical system of claim 1 wherein the computer is further configured to maintain the instrument holder at the second pre-determined distance from the pre-determined bone location while the instrument is translated within the instrument holder.

* * * * *